US007713915B1

(12) United States Patent
Gariepy et al.

(10) Patent No.: US 7,713,915 B1
(45) Date of Patent: May 11, 2010

(54) CYTOTOXIC HETEROMERIC PROTEIN COMBINATORIAL LIBRARIES

(75) Inventors: Jean Gariepy, Toronto (CA); Mark Robert Bray, Toronto (CA)

(73) Assignee: Molecular Templates, Inc., Georgetown, TX (US)

( * ) Notice: Subject to any disclaimer, the term of this patent is extended or adjusted under 35 U.S.C. 154(b) by 602 days.

(21) Appl. No.: 09/601,644

(22) PCT Filed: Dec. 8, 1998

(86) PCT No.: PCT/CA98/01137

§ 371 (c)(1),
(2), (4) Date: Dec. 11, 2000

(87) PCT Pub. No.: WO99/40185

PCT Pub. Date: Aug. 12, 1999

(30) Foreign Application Priority Data

Feb. 4, 1998 (CA) .................................... 2222993

(51) Int. Cl.
*C40B 20/01* (2006.01)
*G01N 33/53* (2006.01)

(52) U.S. Cl. ..................... 506/9; 506/2; 506/4; 506/23; 506/26; 530/350; 536/23.4

(58) Field of Classification Search ..................... 435/6, 435/7.23, 91.53; 506/9, 2, 4, 23, 26; 530/350; 536/23.4
See application file for complete search history.

(56) References Cited

U.S. PATENT DOCUMENTS

| | | | | |
|---|---|---|---|---|
| 4,753,894 | A * | 6/1988 | Frankel et al. | 435/7.23 |
| 5,047,513 | A | 9/1991 | Dobeli et al. | |
| 5,310,663 | A | 5/1994 | Dobeli et al. | |
| 5,354,670 | A * | 10/1994 | Nickoloff et al. | 435/91.53 |
| 5,571,698 | A | 11/1996 | Ladner et al. | |
| 5,659,123 | A * | 8/1997 | Van Rie et al. | 800/302 |
| 5,869,250 | A * | 2/1999 | Cheng et al. | 435/6 |
| 5,888,750 | A | 3/1999 | Vanmaele et al. | |
| 5,922,848 | A | 7/1999 | Vanmaele et al. | |
| 6,086,900 | A | 7/2000 | Draper | |
| 6,833,131 | B1 * | 12/2004 | Smith | 424/130.1 |
| 2002/0161203 | A1 * | 10/2002 | Sheppard et al. | 530/395 |
| 2003/0188326 | A1 * | 10/2003 | D'Andrea et al. | 800/8 |

OTHER PUBLICATIONS

Jackson et al., J. Bacteriol. 172: 653-658 (1990).*
Perera et al., J. Bacteriol. 173: 1151-1160 (1991).*
Smedley et al., Microbiology 142: 1617-1624 (1996).*
Reidhaar-Olson et al., Meth Enzymol (1991), vol. 208: 564-586.*
Janda, K.D. "Tagged versus untagged libraries: Methods for the generation and screening of combinatorial chemical libraries", PNAS USA Nov. 1994, 91, 10779-10785.*
Roberts et al., Mini Reviews in Medicinal Chemistry (2004) vol. 4, pp. 505-512.*
Battelli, Mini Reviews in Medicinal Chemistry (2004) vol. 4, pp. 513-521.*
Hartley et al., Biochimica et Biophysica Acta (2004), 1701, pp. 1-14.*
Kasturi et al., J. of Biol. Chem. Nov. 15, 1992, vol. 267, No. 32, pp. 23427-23433.*
Kaneda, "Gene Therapy: A Battle Against Biological Barriers", Current Molecular Medicine 2001, vol. 1, pp. 493-499.*
Skehan, Philip, et al., New C lorimetric Cytotoxicity Assay for Anticancer-Drug Screening, Articles, vol. 82, No. 13, Jul. 4, 1990, pp. 1107-1112.
Kubota, M.D., Tetsuro, et al., Colorimetric Chemosensitivity Testing Using Sulforhodamine B, Journal of Surgical Oncology 52:83-88 (1993).
Degrandis, Stephanie, et al., Globotetraosylceramide Is Recognized by the Pig Edema Disease Toxin, The Journal of Biological Chemistry, vol. 264, No. 21, Jul. 26, 1989, pp. 12520-12525.
Keusch, Gerald T., et al., Globotriaosylceramide, Gb3, Is an Alternative Fun ctional Receptor for Shiga-like Toxin 2e, Infection and Immunity, Mar. 1995, p. 1138-1141.
T. Iida et al.: "A single amino acid substitution of *Escherichia coli* enterotoxin affects its oligomer formation" J. Biol. Chem., vol. 265, No. 24, Aug. 25, 1989, pp. 14065-14070.
C. Clark et al.: "Phenylalanine 30 plays an important role in receptor binding of verotoxin-1" Molecular Microbiol., vol. 19, No. 4, Feb. 1996, pp. 891-899.

G.J. Tyrell et al.: "Alteration of the carbohydrate binding specificity of verotoxins from Gal(alpha)1-4Gal to GalNAc(beta)1-3Gal(alpha)1-4Gal and vice versa by site-directed mutagenesis of the binding subunit" Proc. Natl. Acad. Sci., vol. 89, Jan. 1992, pp. 524-528.

J.D. Mermes et al.: "A reliable method for random mutagenesis: the generation of mutant libraries using spiked oligonucleotide primers" _Gene, vol. 84, 1989, pp. 143-151.

G. Del Rio et al.: "Combinatorial libraries of proteins: Analysis of efficiency of mutagenesis techniques" Biotechniques, vol. 17, No. 6, 1994, pp. 1132-1139.

A.A. Khine and C.A. Lingwood: "Capping and receptor-mediated endocytosis of cell-bound verotoxin (Shiga-like toxin) 1: Chemical identification of an amino acid in the B subunit necessary for efficient receptor glycolipid binding and cellular internalization" J. Cell Physiol., vol. 161, No. 2, Nov. 1994, pp. 319-332.

(Continued)

*Primary Examiner*—Teresa D. Wessendorf
(74) *Attorney, Agent, or Firm*—Ropes & Gray, LLP; Barbara A. Ruskin; Connie Wong

(57) ABSTRACT

A method is provided for constructing, identifying and using new therapeutic or diagnostic proteins capable of binding to a target cell. The new proteins are derived by mutating a binding subunit of a wild type heteromeric cytotoxic protein to create a library of microorganism clones producing mutant proteins which are then screened for their ability to specifically bind to and kill a target cell.

28 Claims, 6 Drawing Sheets

OTHER PUBLICATIONS

P.-G. Nyholm et al.: "Two distinct binding sites for globotriaosyl ceramide on verotoxins: identification by molecular modelling and confirmation using deoxy analogues and a new glycolipid receptor for all verotoxins" Chemistry and Biology, vol. 3, No. 4, Apr. 1996, pp. 263-275,.

L.P. Perera et al.: "Identification of three amino acids residues in the B subunit of Shiga toxin and Shiga-like toxin type II that are essential for holotoxin activity" J. Bacteriol., vol. 173, No. 3, Feb. 1991, pp. 1151-1160, XP002096325 Am. Soc. Microbiol., Baltimore,US; cited in the application see the whole document.

D.J. Bast et al.: "Toxicity and immunogenecity of a verotoxin 1 mutant with reduced globotriaosylceramide receptor binding in rabbits" Infection and Immunity, vol. 65, No. 6, Jun. 1997, pp. 2019-2028, XP002096326 ASM,Washington,DC,US see the whole document.

M.P. Jackson et al.: "Functional analysis of the Shiga toxin and Shiga-like toxin type II variant binding site subunits by using site-directed mutagenesis" J. Bacteriol., vol. 172, No. 2, Feb. 1990, pp. 653-658, XP002096328 Am. Soc. Microbiol.,Baltimore,US; see the whole document.

S.W. Lindgren et al.: "The specific activities of Shiga-like toxin type II (SLT-II) and SLT-II related toxin of enterohemorrhagic *Escherichia coli* differ when measured by vero cell cytotoxicity but not by mouse lethality" Infection and Immunity, vol. 62, No. 2, Feb. 1994, pp. 623-631, XP002096327 ASM,Washington,DC,US see the whole document.

Bray, M. R. et al: "Expression of the Shiga-like toxin I receptor CD77 on human breast carcinomas, follicular lymphomas and multiple myelomas and absence of expression on CD34+ human hematopoietic cells: Implications for tumor cell purging." Proceedings of the American Association for Cancer Research Annual Meeting, (Mar. 1998), vol. 39, pp. 63. Meeting Info.: 89th Annual Meeting of the American Association for Cancer Research New Orleans, Louisiana, USA Mar. 28-Apr. 1, 1998 American, XP002096336 Abstract No. 429.

Bray, M. R. et al: "Shiga-like toxin as a template for the development of anti-breast cancer agents." Proceedings of the American Association for Cancer Research Annual Meeting, (Mar. 1998) vol. 39, pp. 62-63. Meeting Info.: 89th Annual Meeting of the American Association for Cancer Research New Orleans, Louisiana, USA Mar. 28-Apr. 1, 1998 Americ, XP002096335 Abstract No. 428.

P.G. Nyholm et al.: "Modelling of the interaction of verotoxin-1 (VT1) with its glycolipid receptor. globotriaosylceramide (Gb3)" Int. J. Biol. Macromol., vol. 17, No. 3-4, Jun. 1995, pp. 199-204.

P.E. Stein et al.: "Crystal structure of the cell-binding B oligomer of verotoxin-1 from *E. coli*" Nature, vol. 355, Feb. 20, 1992, pp. 748-750, XP002096334 MacMillan Journals Ltd., London,UK cited in the application see the whole document.

H. Ling et al.: "Structure of the Shiga-like toxin I B-pentamer complexed with an analogue of its receptor Gb3" Biochemistry, vol. 37, Feb. 17, 1998, pp. 1777-1788.

* cited by examiner

1
KEFTLDFSTAKTYVDSLNVIRSAIGTPLQTISSGGTSLLMIDSGSGDNLFAV

DVRGIDPEEGRFNNLRLIVERNNLYVTGFVNRTNNVFYRFADFSHVTFPGT

TAVTLSGDSSYTTLQRVAGISRTGMQINRHSLTTSYLDLMSHSGTSLTQS

VARAMLRFVTVTAEALRFRQIQRGFRTTLDDLSGRSYVMTAEDVDLTLN

WGRLSSVLPDYHGQDSVRVGRISFGSINAILGSVALILNCHHHASRVARM

293
ASDEFPSMCPADGRVRGITHNKILWDSSTLGAILMRRTISS

FIG. 1A 1
              15     19          30 33
TPDCVTGKVEYTK|YNDDDT|FTVKVGDKEL|FTNR|WNLQSLLLSAQITGMTV
      58      64    69
TIKTNAC|HNGGGFS|EVIFR

FIG. 1B

```
                    Acc I                            Loop 1
50-AAG GTG GAG TAT ACA AAA TAT AAT [ NNS NNS NNS NNS NNS ] ACA
GTT AAA
               Sac I          Loop 2
GTG GGT GAT AAA GAA TTA [ NNS NNS NNS NNS ] TGG AAT CTT CAG TCT C
```

FIG. 3A

```
             Pst I
50-TAC GTA CTG CAG CTC CAG TCA ACG AAA AAT AAC TTC GCT GAA TCC
ACC GCC ATT ATG GCA CGC GTT AGT TTT AAT GGT TAC AGT CAT ACC GGT
AAT TTG CGC ACT GAG AAG AAG AGA CTG AAG ATT CC-30
```

FIG. 3B

CYTOTOXIC HETEROMERIC PROTEIN COMBINATORIAL LIBRARIES

CROSS REFERENCE TO RELATED APPLICATION

This application a 371 of PCT Patent Application CA98/01137, which claims priority from Canadian patent application number 2,222,993, filed Feb. 4, 1998, which is pending.

FIELD OF THE INVENTION

The invention relates to methods for identifying new therapeutic or diagnostic proteins capable of binding to a target cell, and uses for those methods.

BACKGROUND OF THE INVENTION

Most present-day chemotherapeutic agents used in controlling eukaryotic cell proliferation (as exemplified by anti-cancer and antifungal agents) tend to be small molecules that are able to perform a single task relatively well, i.e., killing or arresting the proliferation of rapidly dividing cells. Unfortunately, most of these chemotherapeutics possess minimal tissue specificity and non-optimal biodistribution profiles. In addition, the use of cytotoxic or cytostatic drugs in doses sufficient to halt the growth of malignant cells represents a selection pressure that can lead to the appearance of drug resistance mechanisms.

Many plant and bacterial toxins represent successful protein designs able to penetrate mammalian cells and localize themselves into intracellular compartments. These proteins are very effective at deleting target cells or at activating non-lethal cellular processes. The understanding of how such proteins are constructed has increased dramatically in recent years.

A large number of plant and bacterial toxins can be grouped under a common theme of structural organization. They are heteromeric in nature with two or more polypeptide domains or subunits responsible for distinct functions (1). In such proteins, the two or more subunits or domains could be referred to as A and B, and the toxins as $AB_x$ toxins where x represents the number of identical or homologous B subunits in the toxin. This family of framework-related toxins includes examples such as Shiga and Shiga-like toxins, the *E. coli* heat-labile enterotoxins, cholera toxin, diphtheria toxin, pertussis toxin, *Pseudomonas aeruginosa* exotoxin A (2,3) as well as plant toxins such as ricin and abrin. Based on their ability to block protein synthesis, proteins such as Shiga and Shiga-like toxins as well as ricin, abrin, gelonin, crotin, pokeweed antiviral protein, saporin, momordin, modeccin, sarcin, diphtheria toxin and exotoxin A have been referred to as ribosome-inactivating proteins (RIP).

SUMMARY OF THE INVENTION

The present invention utilizes the concept of using a multi-tasking heteromeric protein toxin such as Shiga toxin or other related ribosome-inactivating protein (RIP) as a molecular template in developing powerful cytotoxic agents having the ability to bind specifically to target cells. By modifying residues affecting only the receptor-binding specificity of the toxin template, it is possible in accordance with the invention to use the toxic A toxic domain or subunit present in all mutant toxins as a molecular search engine in screening combinatorial protein libraries of the toxin's template to find mutant toxins that kill specific cells or cell types.

The inventors have thus developed a method for identifying cytotoxic mutant proteins with different receptor-binding specificity than the wild-type toxin by selecting a heteromeric protein toxin, generating a library of microorganism clones producing variant protein toxins by incorporating mutations into the DNA encoding for the binding subunit of the toxin, and screening the library against a population of screening cells by isolating clones or pools of clones producing the variant protein toxins, treating preparations of the population of screening cells with the variant protein toxins produced by the clones or pools of clones, and selecting a cytotoxic mutant protein or pool of cytotoxic mutant proteins that inhibits or kills the population of screening cells. In preferred embodiments, the mutations may be incorporated into the binding subunit by use of a combinatorial cassette method or by means of a unique site elimination method.

In one preferred embodiment, the library thus comprises genetically engineered bacteria or bacterial supernatants containing the variant protein toxins. In another preferred embodiment, the library is made up of genetically engineered yeast or yeast supernatants containing said variant protein toxins.

The toxin may, for example, be selected from a group comprising prokaryotic or eukaryotic proteins or protein fusion constructs capable of blocking protein synthesis. In preferred embodiments, the toxin is selected from a group comprising Shiga toxin, Shiga-like toxins, ricin, abrin, gelonin, crotin, pokeweed antiviral protein, saporin, momordin, modeccin, sarcin, diphtheria toxin and *Pseudomonas aeruginosa* exotoxin A. In further preferred embodiments, the binding subunit is derived from the B-subunit template of either Shiga toxin or related Shiga-like toxins, or homologous counterparts from *E. coli* heat labile enterotoxins, cholera toxin, pertussis toxin or the receptor binding domain of ricin. The target cell may be a tumour cell, for example, a breast cancer cell.

Thus in one embodiment of the invention, it has been shown that a family of related mutant combinatorial toxins, from, for example Shiga toxin or Shiga-like toxin 1, can be derived that can kill breast cancer cells which were previously insensitive to the native toxin.

The invention also provides a method of killing or inhibiting a target cell by treating the target cell with a cytotoxic mutant protein or pool of proteins selected by the methods of the invention. The target cell may be the same as the cells used as the population of screening cells, or it may be a different type of cell which shares a common receptor with the screening cells to which the cytotoxic mutant protein binds. Thus, as noted below, cytotoxic mutant proteins identified using a screening cell population may be further screened against cells from a patient using methods known in the art.

In another embodiment, the invention provides a method for identifying therapeutic proteins having binding specificity for a target cell by selecting a heteromeric protein toxin, generating a library of microorganism clones producing variant protein toxins, screening the library against the population of screening cells by the methods of the invention, and then testing for effectiveness against the target cells (if the target cells are different form the screening cells). To minimize non-specific toxicity, the cytotoxic mutant proteins are further screening against non-target cells to select a therapeutic mutant protein or pool of therapeutic mutant proteins that are less effective at inhibiting or killing the non-target cells than at inhibiting or killing the target cells.

The invention further teaches a method for constructing diagnostic probes for detecting the presence of a cell surface marker by selecting a mutant heteromeric protein toxin by the screening methods of the invention, selecting from the library of microorganism clones a clone which is producing the cytotoxic mutant protein, preparing a diagnostic DNA sequence by incorporating a marker DNA encoding for a detectable marker into a binding subunit DNA sequence in the selected clone and, generating diagnostic probes from the diagnostic DNA sequence. In a preferred embodiment, the marker DNA codes for green-fluorescent protein (GFP).

The invention also teaches methods for constructing a medicament having binding specificity, for example, by selecting by the methods of the invention the cytotoxic mutant protein, selecting from the library of microorganism clones a clone which is producing the cytotoxic mutant protein, preparing a medicament DNA sequence by incorporating medicinal polypeptide DNA encoding for a medicinal polypeptide into a binding subunit DNA sequence in the selected clone and, generating a medicament from the medicament DNA. The medicaments of the invention may be used for treating a condition requiring targeting a medicine to a target cell occurring in a host organism.

In other embodiments, the invention provides kits useful for performing the methods of the invention, the kits including a selected heteromeric protein toxin and suitable supports useful in performing a method of the invention.

BRIEF DESCRIPTION OF THE DRAWINGS

FIG. 1 is the amino acid sequences of the A subunit (FIG. 1A; corresponding to SEQUENCE ID. NO. 1) and B (FIG. 1B; corresponding to SEQUENCE ID. NO. 2) subunit of Shiga-like toxin 1.

FIG. 3 is the oligonucleotide sequences of Primer A (FIG. 3A; corresponding to SEQUENCE ID. NO. 3) and Primer B (FIG. 3B; corresponding to SEQUENCE ID. NO. 4) synthesized for creation of the ShT libraries.

DETAILED DESCRIPTION OF THE PREFERRED EMBODIMENT

Figure 2C:
FIG. 2 shows backbone representations of Shiga toxin (ShT; panel A, side view) and its B subunit (panels B and C, bottom view).

The present inventors have constructed protein combinatorial libraries based on the structural template of a heteromeric protein toxin for use in deriving toxin mutants with receptor specificities directed at targets resistant to the native toxin. The strength of this new approach stems from the fact that all members of these libraries are cytotoxic in nature. This common property of all toxin variants can thus be used as a search engine in finding mutants in these libraries with new receptor specificity. The screening strategy involves the use of simple cell cytotoxicity assays, which immediately identify optimized therapeutic as well as diagnostic agents, thus eliminating the need to redesign any lead compounds to enhance their cellular uptake, intracellular processing and/or cytotoxicity.

Heteromeric plant and bacterial toxins have a structural organization with two or more polypeptide domains or subunits responsible for distinct functions, referred to as A and B. The toxins may be referred to as $AB_x$ toxins where x represents the number of identical or homologous B subunits in the toxin. This family of framework-related toxins includes examples such as Shiga and Shiga-like toxins, the *E. coli* heat-labile enterotoxins, cholera toxin, diphtheria toxin, pertussis toxin, *Pseudomonas aeruginosa* exotoxin A (2,3) as well as plant toxins such as ricin and abrin.

Based on their ability to block protein synthesis, proteins such as Shiga and Shiga-like toxins as well as ricin, abrin, gelonin, crotin, pokeweed antiviral protein, saporin, momordin, modeccin, sarcin, diphtheria toxin and exotoxin A have been referred to as ribosome-inactivating proteins (RIP). The potency of RIPs is exceedingly high; one molecule of diphtheria toxin A chain (99) or ricin A chain (100) having been shown to be sufficient to kill a eukaryotic cell. The crystal structures for many of these molecules have now been established (4-12), and insights into their functions have mostly focused on the identification of residues involved in the catalytic activity of A chains and on mapping B subunit residues involved in receptor-binding activity.

The data presented herein support the broad potential of combinatorial Shiga toxin libraries (or libraries of any heteromeric, cytotoxic member) as sources of potentially cell-specific cytotoxic and diagnostic agents. Since the receptor binding potential of combinatorial proteins such as Shiga toxin (B-subunit pentamer) can be dissociated from its cytotoxic A subunit, the present invention also provides a method for developing non-cytotoxic, diagnostic probes for detecting the presence of useful cell surface markers to aid in the selection of therapeutic strategies. Furthermore, because the binding unit of combinatorial proteins is genetically discrete from the toxin subunit, selected mutant binding units can be produced independently of the toxin subunit, and can be incorporated with marker DNA or therapeutic DNA to create diagnostic probes or cell-specific therapeutic proteins.

The invention thus provides a method for identifying and producing therapeutic or diagnostic proteins capable of binding specifically to a target cell, which said proteins are derived from a wild type heteromeric protein having a cell surface binding domain or subunit and a cytotoxic domain subunit, comprising the steps of: a) creating libraries of mutant heteromeric proteins in which the cell binding domain or subunit has been randomly mutated; and b) screening the library using the cytotoxic domain present in all mutant toxins as a built-in search engine against a population of screening cells which is lacking or has lower levels of receptors which cause sensitivity to the wild type protein, and identifying those mutants which kill the screening cells. As used herein, the term "substantially insensitive" refers to cells useful as screening cells as a result of such a lack of receptors recognized by the wild-type toxin, or the presence of a sufficiently reduced level of such receptors that the activity of the wild-type toxin and the mutant toxin can be distinguished.

The invention also provides a method for constructing and screening therapeutically useful toxin variants that will bind to surface markers (glycolipids, glycoproteins, or proteins, as examples) expressed on human tumour cells in preference to normal cells. The invention further teaches a method for constructing and screening toxin variants which target a defined eukaryotic cell populations such as pathogenic fungi or which can be used to control the growth of rapidly proliferating cells (implicated in scar management, tissue remodelling, or skin diseases for example). Further, the invention teaches a method for constructing and screening therapeutically useful non-cytotoxic, diagnostic probes for detecting the presence of useful cell surface markers to aid in the selection of therapeutic strategies. Shiga toxin variants can subsequently be modified by dissociation of the variant from its cytotoxic subunit or by inactivation of the variant's cytotoxic subunit, or the DNA encoding for the binding subunit of selected variants can be used to construct various diagnostic or therapeutic tools.

The construction of heteromeric protein toxin libraries allows those skilled in the art to rapidly identify new cytotoxic/diagnostic probes with altered receptor targeting properties. The procedure is exemplified herein with reference to Shiga toxin and Shiga-like toxin. Since the natural receptor for the B subunit of Shiga toxin is a glycolipid, the specificity of mutant B subunits derived from Shiga libraries harbouring a low level of degeneracy in the sequence of its loops (which are structures implicated in receptor specificity) may be directed at unique carbohydrate structures located on glycoproteins or glycolipids. In the case of toxin libraries containing highly degenerate sequences within the two loop regions known to mediate binding, it is expected that the potential surface structures recognized will be very diverse. As in the case of antibody combining sites, B subunit variants may bind to a spectrum of molecular entities such as proteins, peptides, nucleic acids or even organic moieties rather than to sugars or glycolipids.

The construction of cytotoxic heteromeric libraries offers several distinct advantages. Firstly, the libraries are permanent and can be indefinitely screened to provide a continual source of new therapeutic or diagnostic agents. Secondly, the lethal character of the resulting toxin mutants towards eukaryotic cells allows one to easily screen for useful constructs having a specificity for unique cell targets (such as cancer cells). Thirdly, useful mutant B subunits can be generated in the absence of a cytotoxic A chain, permitting the immediate creation of non-cytotoxic diagnostic agents that can be used to detect the presence of unique markers on cell types in either in vitro or in vivo settings.

A person skilled in the art will appreciate that the methods of the present invention can be applied to immunotoxins and related growth factor-toxin conjugates to develop multi-tasking agents able to provide more guided therapies or to be utilized as diagnostic tools for cancer and other patients.

For example, concerning therapeutic tools, the present invention presents a method for identifying therapeutic proteins having binding specificity for a target cell for the purpose of developing novel peptide or protein drug delivery vehicles and targeting systems. Having selected an appropriate heteromeric protein toxin having a toxic subunit and a binding subunit, the methods taught herein and adapted, if necessary, by means known in the art, may be used to generate a library of microorganism clones producing variant protein toxins, by incorporating mutations into the binding subunit DNA encoding for the toxin in a microorganism. The library is then screened by methods such as those set out above to select clones or pools of clones producing the cytotoxic mutant proteins which inhibit or kill a population of screening cells. The selected cytotoxic mutant proteins may optionally be further screened against cells from a patient using methods known in the art, by treating preparations of such cells with clones or pools of clones producing cytotoxic mutants, and selecting a cytotoxic mutant protein or pool of cytotoxic mutant proteins that are effective at inhibiting or killing target cells and are safe for the patient.

As another example, the toxic domain or subunit could be modified or replaced with another toxic domain or subunit, selected or engineered such that the toxin requires a co-factor or the like to be activated. In this manner, the therapeutic protein may be administered to a host, and after sufficient time has passed to allow the therapeutic protein to adhere to the target cells, the cofactor can be introduced to the host, thus killing or inhibiting the target cells.

Concerning the construction of diagnostic tools, the methods of the invention provide for selecting a heteromeric protein toxin and generating a library of microorganism clones producing variant protein toxins from the heteromeric protein toxin, for the screening and selection of a mutant toxin with enhanced sensitivity and selectivity. The library is then screened against a population of screening cells by the methods of the invention, i.e. by isolating clones or pools of clones producing the variant protein toxins, treating preparations of the population of screening cells with the variant protein toxins and selecting a cytotoxic mutant protein or pool of cytotoxic mutant proteins that inhibits or kills the population of screening cells. If desired to alleviate toxicity, for example where the selected diagnostic tool is to be used in vivo, one skilled in the art may modify the cytotoxic mutant protein or pool of proteins by dissociation of the binding subunit from the toxic subunit or by inactivation of a toxic subunit of the cytotoxic mutant protein. One may additionally, if needed, label the cytotoxic mutant protein or pool of proteins with a detectable marker. Alternatively, the genes producing the cytotoxic mutant protein or pool of proteins are manipulated to endogenously produce detectable markers. For example, the invention is used to construct diagnostic probes for detecting the presence of a cell surface marker by first identifying by the methods taught herein a cytotoxic mutant protein or pool of proteins, and subsequently preparing a diagnostic DNA sequence by incorporating, by any means known in the art, a marker DNA encoding for a detectable marker into the binding subunit DNA sequence(s) of the cytotoxic mutant protein or pool of proteins, and generating diagnostic probes from the diagnostic DNA sequence. Examples of detectable markers known in the art include various enzymes, fluorescent materials, luminescent materials and radioactive materials. Examples of suitable proteins include horseradish peroxidase, variants of green fluorescent proteins, luciferase, alkaline phosphatase or acetylcholinesterase. Examples of suitable fluorescent materials include umbelliferone, fluorescein, dansyl chloride or phycoerythrin. An example of a suitable luminescent material includes luminol. Examples of suitable radioactive materials include P-32, S-35, Cu-64, Ga-67, Zr-89, Ru-97, Tc-99m, In-111, I-123, I-125, I-131, Re-186 and Au-199. The proteins may also be labelled or conjugated to one partner of a ligand binding pair. Representative examples include avidin-biotin and riboflavin-riboflavin binding proteins. Methods for conjugating or labelling the proteins discussed above with the representative labels set forth above may be readily accomplished using conventional techniques.

The invention further presents a method for treating a condition requiring targeting a medicine to a target cell occurring in a host organism. This may be accomplished by use of the methods set out above in selecting a therapeutic protein having binding specificity and subsequently modifying the therapeutic protein by conjugating a medicine (such as a toxin) to the binding subunit of the protein to form a peptide/protein drug delivery vehicle, and administering same to a host organism having a disease associated with the target cell an effective amount of that drug. In the use of this invention to treat a condition, one skilled in the art may optionally further modify the therapeutic protein by the various methods discussed herein.

Further, the invention comprises kits to assist one in carrying out the methods of the invention. Reagents suitable for applying the methods of the invention may be packaged into convenient kits providing the necessary materials, and packaged into suitable containers, optionally containing suitable supports useful in performing the methods of the invention.

Mode of Action of Shiga and Shiga-Like Toxins

Shiga toxin (ShT) and Shiga-like toxins (SLT) are structurally related bacterial toxins involved in the pathogenesis of bacillary dysentery, hemorrhagic colitis, the hemolytic uremic syndrome, and thrombotic thrombocytopenic purpura (19-21). Shiga toxin, the first member of this family of cytotoxins to be reported in 1903 (22,23) is produced by *Shigella dysenteriae* I. Shiga-like toxins have been recently identified as virulence factors elaborated by enterohemorrhagic strains of *E. coli* (24-28). In particular, the *E. coli* strain O157:H7, which produces Shiga-like toxin 1, has been recently identified as the causative agent responsible for recent mass outbreaks of food poisoning in Japan and the United States.

Shiga (ShT) and Shiga-like (SLT) toxins possess the smallest known B subunit (less than 70 residues) of all $AB_x$ toxins, and their A subunit has an identical catalytic activity as the corresponding subunit in ricin. FIG. 1 shows the amino acid sequences of the A and B subunits of Shiga-like toxin 1. Panel A (corresponding to SEQUENCE ID. NO. 1) shows the catalytic A subunit. Panel B (corresponding to SEQUENCE ID. NO. 2) shows the B subunit with the three boxed regions representing loops harbouring residues postulated to be involved in creating a receptor binding cleft for CD77.

Figure 2A:
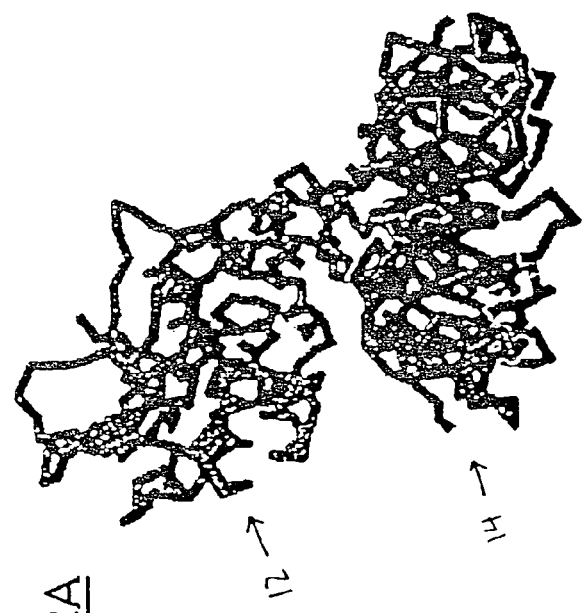
Figure 2B:
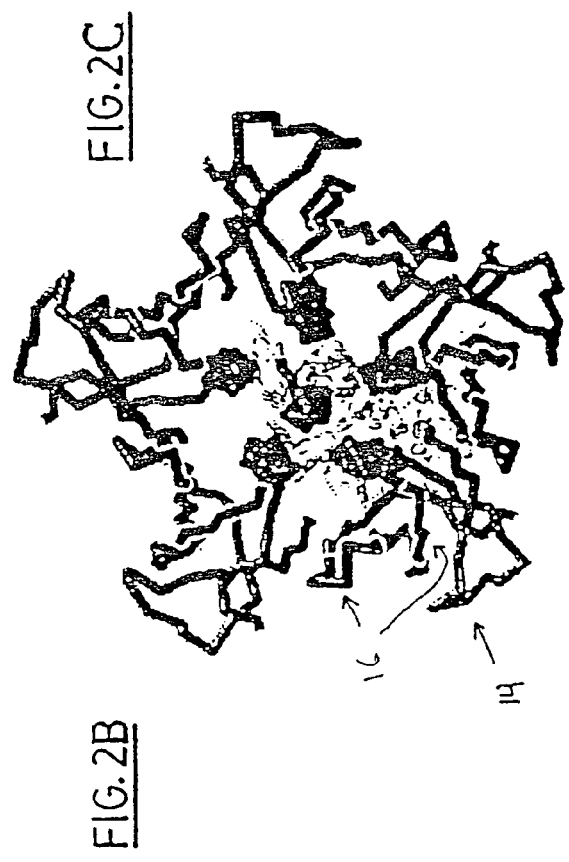

FIG. 2 shows backbone representations of Shiga toxin (ShT; panel A, side view) and its B subunit (panels B and C, bottom view). As seen in FIG. 2, ShT and SLT-1 have identical B subunits. The catalytic A subunit (12, Panel A) has its C-terminus inserted into the central hole of the B subunit pentamer (14). The B subunit pentamer (14, Panel B) is stabilized by intra- and inter-subunit interfaces involving β-sheets. Two of the three loop regions of the B subunit boxed in FIG. 1 (residues 15-19 and 30-33) are darkened (16) to show the orientation and location of these loops in relation to the β-strand structure of the B subunit and the A chain itself. Loop 58-66 is located in the same vicinity as loops 15-19 and 30-33 and was not highlighted for reasons of clarity. In Panel C, each identical B subunit is shaded differently to illustrate their symmetrical arrangement giving rise to a pentamer.

These toxins are proteins composed of six subunits; one catalytic A subunit (293 amino acids; MW 32,317) involved in the blockage of protein synthesis and five B subunits (69 amino acids; MW 7600 each) necessary for the attachment of the toxin to cells (29-35; FIG. 2). The B subunits spontaneously assemble into a pentamer in solution (FIG. 2, panels B and C). The structure of these toxins typifies a common motif employed by other larger bacterial toxins such as cholera toxin and the *E. coli* heat-labile enterotoxins (6,7) and pertussis toxin (8).

The cell specificity of ShT and SLT-1 is encoded by its B subunit which recognizes the glycolipid globotriaosyl ceramide (referred to as CD77 or $Gb_3$; Galα1-4Galβ1-4Glcβ1-1 Ceramide; ref. 36,37). CD77 has a relatively limited tissue distribution, and is expressed on a number of human cancers (13, 102-105). The native toxin has recently been shown to be effective in purging, a human lymphoma from bone marrow (13). Following its attachment to susceptible cells, Shiga toxin is endocytosed from coated pits (38-40). The A-chain is processed to a smaller 27 kDa A₁ fragment through a selective nicking and reduction of the native chain. The $A_1$ fragment is responsible for the inactivation of eukaryotic ribosomes (29) acting as a highly specific N-glycosidase which cleaves a single adenine residue from 28S rRNA (41,42). Depurination at that site inhibits peptide elongation by preventing the EF-1 dependent binding of aminoacyl tRNA to the 60S ribosomal subunit (43-45).

EXAMPLE 1

Designing Shiga Toxin Libraries to Derive Useful Diagnostic and Therapeutic Agents Targeted at Defined Eukaryotic Cell Populations In accordance with the invention, the receptor specificity of the toxin, which is encoded by its B subunit, was altered by random mutagenesis. Mutations in the B subunit were kept to a minimum in order to lessen any negative effects on other functions of the toxin such as the toxicity of its A chain and the proper folding and assembly of the holotoxin (i.e., pentamerization of the B subunit, insertion of the $A_2$ domain into the B pentamer, exposure and orientation of the protease sensitive loop, and packing environment of the translocation domain).

Shiga and Shiga-like toxin 1 have identical B subunits. The B subunit is a small protein composed of only 69 amino acids that pentamerizes spontaneously in solution. Its crystal structure (as a pentamer of B subunits) has been solved in the presence and absence of the A subunit (4,5) and has been shown to be identical in either context. Each B subunit monomer within the pentameric structure is composed of 6 β-strands (β1, residues 3-8; β2, residues 9-14; β3, residues 20-24; β4, residues 27-31; β5, residues 49-53; β6, residues 65-68) involving 31 of its 69 amino acids (45%; FIG. 2). A single α-helix (residues 36 to 46) accounts for 16% of the remaining structure. These elements of secondary structure appear essential for the maintenance of the pentamer integrity and its association with the $A_2$ domain of the A chain (FIG. 2). Thus, any perturbations in these regions may result in folding problems. Three loop regions composed of more than two amino acids are left. They are delimited by residues 15 to 19, 32 to 35, and 54 to 64, respectively. Mutagenesis studies of the B subunit have indicated that substitutions at positions 16, 17, 30, 33, and 60 either abolished or reduced the cytotoxic potential of the resulting toxin while an Asp to Asn substitution at position 18 altered the receptor specificity of the toxin (85-89). Molecular modelling studies involving the docking of CD77 ($Gb_3$) to the B subunit have implicated residues located in these loops (90,91). It has been hypothesized that there are two potential binding sites for CD77 on the B subunit pentamer, namely, sites I and II (90,91). Residues located in regions 15-19 and 30-33, in particular Asn15, Asp 16, Asp 17, and Phe 30, form most of the putative binding site I (91). The calculated interaction energy derived from modelling studies suggested that site I is likely to be the predominant site mediating CD77 interaction (91). Thus, results from both site-directed mutagenesis and docking experiments suggest that residues found in loop regions are sites where random mutagenesis may lead to an altered receptor specificity. As described herein, residues are perturbed within two loop regions, namely, residues 15-19 (loop 1), and residues 30-33 (loop 2; technically speaking, this region is not a loop but rather represents the end of the β4 strand and the beginning of the second loop). Random mutagenesis in loop 3 (residues 58-64; FIG. 2) may also be effective in achieving the objective of the invention. Though initial studies have focussed on the aforementioned regions of the molecule, this delimitation does not preclude the possibility of targetting any of the B subunit residues in attempts to alter specificity of the toxin.

Nine residues are involved in loops 1 and 2, creating a potential library complexity of the order of $20^9$ ($5 \times 10^{11}$ different mutant proteins, if all nine residues were totally randomized and all potential combinations recovered). It is, therefore, advantageous to reduce the level of complexity of the toxin library so that the nine residues of interest are not completely randomized. This goal was accomplished by synthesizing oligonucleotides for use in the mutagenesis procedure that have increasing levels of nucleotide "doping". The selection of an oligonucleotide with the desired level of doping for mutagenesis subsequently allows direct control over the level of diversity in the library made from that particular oligonucleotide pool. For example, mutations at 5 amino acid positions out of 9 in the target region, would yield a diversity of the order of $20^5$ ($3.2 \times 10^6$ mutant toxins), a more satisfactory level of diversity. Indeed, the screening of libraries with greater than $10^6$ compounds has not previously proven necessary for chemical or peptide libraries in terms of identifying useful "lead" compounds (using either binding assays or functional assays in the screening process). Additionally, the number of potential target sites on cell surfaces will be large and will increase the need for screening steps.

EXAMPLE 2

Mutagenesis and Construction of Heteromeric Cytotoxic Protein Combinatorial Libraries Shiga and Shiga-like toxin 1 differ in sequence by only one amino acid in their A subunit and have identical B subunits. Although the random mutagenesis procedures described herein use the SLT-1 gene, the simpler terminology "Shiga toxin library" has been used rather than "Shiga-like toxin 1 library" in defining an ensemble of mutant proteins derived from the Shiga toxin structural template.

Briefly, the recombinant plasmid pJLB28 (32) was used as a template for mutagenesis. This construct carries a BglII-BalI fragment of bacteriophage H-19B inserted in pUC19, which specifies for the production of active SLT-1 holotoxin. An additional construct was made by cloning a PCR product consisting of the SLT-1 gene carried by pJLB28 into the prokaryotic expression vector pTUG (92). The latter construct, pTGXH, encodes for the production of SLT-1 with a hexa-histidine sequence fused to the N-terminus of the A chain, to facilitate the purification of toxin variants.

There are numerous methods available for generating random mutations in DNA. Mutagenesis using synthetic oligonucleotides with regions of defined degeneracy (93-96) is an established and reliable technique which satisfies the requirements of the invention, i.e., a rigidly defined mutagenic window and the need to control the frequency and type of mutations generated. Mutagenic oligonucleotides (98-mers) with the sequence indicated in FIG. 3 were synthesized on an Applied Biosystems 392 DNA synthesizer. Loop 1 and loop 2 represent residues 15-19 and 30-33 of the B subunit, respectively. Primer A (FIG. 3A; corresponding to SEQUENCE ID. NO. 3) was synthesized to have controlled levels of randomization in the two loops as described in the text. Primer B (FIG. 3B; corresponding to SEQUENCE ID. NO. 4) overlaps primer A by 15 bases at its 3' end, and was used to create a combinatorial cassette by mutually primed synthesis in conjunction with primer A. Restriction sites used to clone the libraries are indicated in bold. The primers were designed to mutagenize both loops 1 and 2 simultaneously. A silent mutation introducing a new Sac I restriction site between the two zones was incorporated into the mutagenic primer to facilitate screening of transformant DNA and to allow for the "shuffling" of zones between variants. Five different (98-mers) mutagenic primers were synthesized with increasing levels of "randomness" in loops 1 and 2, so that libraries of predictable size could be generated. This strategy was accomplished by synthesizing codons in the loop regions in the form "NNS", where N is a base added to the growing chain from a mixture of the wild-type base "doped" with a fixed percentage of the three other bases, and S is a base added from a 1:1 mixture of cytosine and guanine. The latter aspect of the method allows codons specifying all 20 amino acids, but makes the chances of observing a given amino acid closer to 1:20 by reducing the degeneracy of the DNA code. Also, only the amber stop codon TAG can be generated using this strategy; thus, minimizing the production of truncated proteins.

The five mutagenic primers synthesized had doping levels ranging from 1.2% to 75%, where 75% represents completely random codons (i.e., the phosphoramidite mixture used to place the given base contained 25% wild-type bases and 25% each of the other bases). A mutagenic primer made with a 12.5% doping level was chosen for initial studies to produce a library where the number of potentially different sequences ($3.2\times10^6$ mutants, or a mutation rate of approximately 5 substitutions out of 9 per clone) was well within the limits of *Escherichia coli* transformation efficiency.

Two strategies have been employed so far to incorporate the mutagenic oligonucleotides into the toxin gene to create libraries of variant proteins; using the unique site elimination method (97) or by creating a combinatorial cassette. Single-stranded random mutagenic primers were incorporated into double-stranded plasmids using the unique site elimination (USE) mutagenesis method (97) employing the Pharmacia USE kit. This method allows mutagenesis to be performed on any double-stranded plasmid in the absence of restriction sites (97).

In an attempt to increase the efficiency of the mutagenesis procedure and to maximize the diversity of clones obtained, a combinatorial cassette method has also been employed to generate toxin libraries. In this method, the same oligonucleotide pools depicted in FIG. 3A were annealed to an overlapping oligo sequence shown in FIG. 3B. A double-stranded cassette was created by mutually primed synthesis, i.e., by including DNA polymerase and dNTP's in a reaction with the overlapping pair such that each oligonucleotide would code for the formation of the opposite sense strand. The cassette was then amplified using PCR and cloned directly into the vector containing the toxin gene at sites AccI and PstI.

Further refinements to the mutagenic process are known to those in the art. For example, libraries may be created using an entirely ligation-free system employing the uracil DNA glycosylase method (101). Notably, the demonstrated ability to use the same random oligonucleotide pools in a variety of different mutagenesis procedures underscores the flexibility of the system and its high capacity for adaptation and rapid improvement.

EXAMPLE 3

Screening of Heteromeric Cytotoxic Protein Combinatorial Library Against Breast Cancer Cell SK-BR-3

An initial library was constructed using the USE method with a mutagenic oligonucleotide with a 12.5% doping level. Following transformation of *E. coli* strain JM101 with vector DNA within which the randomized oligonucleotide had been incorporated, colonies picked from agar plates were grown in 96-well plates with conical well-bottoms and individual clones were picked from isolates. To confirm that the variants were producing toxin with an A chain capable of inactivating ribosomes, extracts produced by 17 clones selected at random were collected and assayed for their ability to inhibit eukaryotic protein synthesis. This assay uses Promega TnT coupled transcription/translation reticulocyte lysate system, and consists of measuring the product of a luciferase gene in the presence and absence of bacterial extracts. The extracts of all the clones tested inhibited translation of the luciferin protein. Five of these variants were sequenced, and the nucleotide sequences of the randomized loop regions are listed in Table 1. The tested clones reflected the desired rate of mutation of approximately 5 out of 9 amino acid changes per clone.

Table 1—Nucleotide and Amino Acid Sequences of ShT Mutant Clones and Wild-Type Shiga Toxin Skehan, et al., *J. Nat. Cancer Inst.* 82, 1107 (1990)]. Sib selection [M. McCormick, *Meth. Enzmol.* 151, 445 (1987)] was employed when screening ShT clones. When clones that killed the target cells were identified, they were inoculated into 3 ml of TB-carb, grown overnight at 37° C. with shaking at 250 rpm and then extracted and re-tested for cytotoxicity against the cell line.

A set of 1000 clones were picked from the (12.5% doping) library to test the screening strategy. An 8×8 sib selection grid system (98) was used, whereby a given clone was pooled with seven others in a system where every clone tested was present in two separate pools. The 8-clone pools were amplified and then extracts from the mixtures were tested for cytotoxicity on Vero cells (a cell line highly susceptible to the wild-type toxin) and the human breast cancer SK-BR-3 cell line (a cell

| Clone | Loop 1 | | | | | | Loop 2 | | | | | Mutation Rate |
|---|---|---|---|---|---|---|---|---|---|---|---|---|
| Wild-type | AAT | GAT | GAC | GAT | ACC | Seq ID No 5 | TTT | ACC | AAC | AGA | Seq ID No 6 | |
| | N | D | D | D | T | Seq ID No 7 | F | T | N | R | Seq ID No 8 | |
| ShT 6 | AAC | GAG | GAG | GAG | ACG | Seq ID No. 9 | TTC | GCG | AAC | AGC | Seq ID No 11 | 5/9 |
| | N | E | E | E | T | Seq ID No 10 | F | A | N | N | Seq ID No 12 | |
| ShT 13 | AAC | GAG | CAG | GAC | ACC | Seq ID No 13 | TTC | ACC | CAC | AGG | Seq ID No 15 | 3/9 |
| | N | E | Q | D | T | Seq ID No 14 | F | T | H | R | Seq ID No 16 | |
| ShT 15 | AAG | GAG | AAC | GAG | AGC | Seq ID No 17 | TTC | GCG | AAC | AAC | Seq ID No 19 | 7/9 |
| | K | E | N | E | S | Seq ID No 18 | F | A | N | N | Seq ID No 12 | |
| ShT 17 | AAG | GAC | GAC | GCG | AGG | Seq ID No 20 | TTG | ACC | CAG | AGG | Seq ID No 22 | 5/9 |
| | K | D | D | A | R | Seq ID No 21 | L | T | Q | R | Seq ID No 23 | |
| ShT 19 | AAG | GAC | GAC | GAC | ACG | Seq ID No 24 | TTG | ACC | CAG | AGG | Seq ID No 22 | 3/9 |
| | K | D | D | D | T | Seq ID No 25 | L | T | Q | R | Seq ID No 23 | |

Table 1. Comparison of nucleotide and amino acid sequences between mutagenic loops of five ShT mutant clones recovered from one of our ShT combinatorial libraries (12.5% doping level) and wild-type Shiga toxin. Loops 1 and 2 represent residues 15-19 and 30-33 of the B subunit of ShT (or SLT-1) respectively.

The ability of a ShT variant to kill cells represents the most direct and practical measure of its utility. This function (cytotoxic property retained by all toxin variants) provides each mutant with a built-in search engine allowing one to screen any ShT combinatorial libraries against any eukaryotic cells to identify novel mutant toxins that can kill such cells.

In one example, the breast cancer cell line SK-BR-3 is used as the initial eukaryotic population of screening cells. SK-BR-3 cells were obtained from the American Type Culture Collection. Cells were grown and maintained in α-MEM media supplemented with 10% fetal calf serum. Cells were grown at 37° C., 5% $CO_2$ and the media changed every 2 days. Cell densities were chosen to ensure that each cell line was at approximately the same degree of confluency at the beginning of a cytotoxicity assay.

Toxin-containing extracts were produced by freeze-thawing [B. H. Johnson, M. H. Hecht, *Bio/Technology* 12, 1357 (1994)] pellets from overnight cultures of individual clones of *E. coli* strain JM101 transformed with mutagenized vector DNA. The clones were grown in either 200 μl (clones screened on SKBR-3) or 800 μl (clones screened on CAMA-1) of Terrific broth supplemented with 100 mg/ml carbenicillin (TB-carb). Extracts were allowed to intoxicate the breast cancer cells for 48 hours, then cell viability was measured using either the tetrazolium salt WST-1 (4-[3-(4-Iodophenyl)-2-(4-nitrophenyl)-2H-5-tetrazolio]-1,3-benzene disulfonate; Boehringer Mannheim), or by measuring total cellular protein content using the dye sulforhodamine B (SRB) [P.

line that is insensitive to the wild-type toxin). A colorimetric assay based on the cleavage of the tetrazolium salt WST-1 by mitochondrial dehydrogenases in viable cells was used to quantify cell viability. The cleavage of WST-1 gives rise to a water-soluble formazan that can be readily measured in the visible range (450 nm) using a 96-well plate format and a plate reader, thus allowing the use of high throughput screening approaches. Other colorimetric cell viability assays were or could be used such as alternate tetrazolium salts XTT, MTT, or dyes such as sulforhodamine B. In addition, screening could be performed using cell proliferation assays measured in terms of counting cell colonies or the incorporation of radiolabeled nucleotides or amino acids into nucleic acids or proteins. Clones that were implicated in producing cell-killing toxins were retested individually on the same cell lines. This preliminary set of clones has yielded thus far at least 14 clones that show a dramatic increase in their ability to kill SK-BR-3 cells relative to the wild-type ShT. Several lysates were able to delete z 90% of SK-BR-3 cells in relation to control wells containing viable cells (no toxin present). Plasmid DNA was recovered and sequenced from isolates that consistently killed SK-BR-3 cells in cytotoxicity assays. Sequence alignments in the mutated B-subunit loop regions of 14 mutant toxins are presented in Table 2.

Several clones showed reduced cytotoxicity on Vero cells but enhanced SK-BR-3 toxicity. The latter clones are of significant interest, since the goal of the invention is to alter the natural specificity of the toxin from the CD77 glycolipid to another cell surface marker. Scaling up the screen to greater than 1000 single clones optimizes the screening strategy.

The clones identified from this low-level degeneracy library show a marked conservation of the first loop (residues 15 to 19), which may reflect a "skewing" of the isolates recovered towards ShT mutants able to bind to receptor homologs of CD77. In contrast, clones picked at random from the same library did not show any predisposition toward maintenance of the wild-type sequence, and had amino acid substitutions in their target regions at the predicted rate (results not shown). Several of the cytotoxic ShT variants were overexpressed, purified to homogeneity and assessed for their cytotoxicity against SK-BR-3 cells.

Table 2—SK-BR-3 Library

| Clone | Loop 1 | | Loop 2 | |
|---|---|---|---|---|
| wild-type | N D D D T | Seq ID No 7 | F T N R | Seq ID No. 8 |
| ShT 66 | N E E E T | Seq ID No 10 | E F T G | Seq ID No. 26 |
| ShT 110 | N D D D T | Seq ID No 7 | F T K S | Seq ID No. 27 |
| ShT 128 | T T D D P | Seq ID No 28 | G T R G | Seq ID No. 29 |
| ShT 220 | N D D D T | Seq ID No 7 | L T N G | Seq ID No. 30 |
| ShT 241 | N D D D T | Seq ID No 7 | F T K S | Seq ID No. 27 |
| ShT 256 | N D D D T | Seq ID No 7 | L P N R | Seq ID No. 31 |
| ShT 265 | N D D D T | Seq ID No 29 | F T N C | Seq ID No. 38 |
| ShT 415 | K E D E S | Seq ID No 33 | L T K R | Seq ID No. 34 |
| ShT 506 | N D D D T | Seq ID No 7 | L T K S | Seq ID No. 35 |
| ShT 619 | Y D D N P | Seq ID No 36 | L T N S | Seq ID No. 37 |
| ShT 766 | N D D D T | Seq ID No 7 | L T K R | Seq ID No. 34 |
| ShT 767 | K K E E P | Seq ID No 38 | C A N R | Seq ID No. 39 |
| ShT A22 | N D D D T | Seq ID No 7 | L T K R | Seq ID No. 34 |
| ShT A25 | N D D D T | Seq ID No 7 | L T N R | Seq ID No. 40 |

Table 2. Amino acid sequences of clones exhibiting cytotoxic activity on SKBR-3 cells (recovered from a 12.5% doping level library) and CAMA-1 (clones recovered from a 75% doping level library). Loops 1 and 2 represent the same B subunit residues indicated in Table 1.

EXAMPLE 4

Screening of Heteromeric Cytotoxic Protein Combinatorial Library Against Breast Cancer Cell Line CAMA-1

A second library, this time using an oligonucleotide pool with a more degenerate doping level of 60%, was created using the combinatorial cassette method described previously. The library was screened essentially as the first using the sulforhodamine B cell viability assay and the cell line CAMA-I as the population of screening cells. This cell line is also a breast carcinoma like SKBR-3, but has been shown to lack the CD77 marker and is extremely resistant to the native SLT-1 toxin. CAMA-1 cells were obtained from the American Type Culture Collection. Cells were grown and maintained in α-MEM media supplemented with 10% fetal calf serum. Cells were grown at 37° C., 5% $CO_2$ and the media changed every 2 days. The cell densities were chosen to ensure that each cell line was at approximately the same degree of confluency at the beginning of a cytotoxicity assay.

A collection of 600 SK-BR-3 single clones from the cassette library were screened for cytotoxic effect on CAMA-I, and as in the case of SKBR-3 several promising toxin variants were identified, whose sequences are shown in Table 3. The clones identified from this highly diverse library were found to have amino acid sequences in the target regions which were almost completely different from those in the wild type toxin. The sequence diversity of this library is very large (up to $20^9$ mutants) and exceeds the transformation efficiency limits of *Escherichia coli*) (~$10^{10}$). Cytotoxicity curves for three ShT mutants derived from this screening are presented in FIG. 6. $CD_{50}$ values ranging from 100 to 300 nM were calculated for these ShT variants (variants 122, 126 and 824; cell passage #13; symbols: native toxin (Δ); ShT variant 122 (♦); ShT variant 126 (●); ShT variant 824 (■). Each point represents the percent cell viability calculated from the average of experiments performed in triplicate.

Table 3—CAMA-1 Library

| Clone | Loop 1 | | Loop 2 | |
|---|---|---|---|---|
| wild-type | N D D D T | Seq ID No 7 | F T N R | Seq ID No 8 |
| ShT 122 | C L L N G | Seq ID No 41 | Y Q E P | Seq ID No 42 |
| ShT 126 | Q G L Q L | Seq ID No 43 | T L T G | Seq ID No 44 |
| ShT 142 | T G A T M | Seq ID No 45 | P T G I | Seq ID No 46 |
| ShT 241 | F R P A G | Seq ID No 47 | L R C G | Seq ID No 48 |
| ShT 308 | P Y V F L | Seq ID No 49 | M V A N | Seq ID No 50 |
| ShT 324 | K S M D Q | Seq ID No 51 | L S K W | Seq ID No 52 |
| ShT 715 | Q G E Y G | Seq ID No 53 | I Q E R | Seq ID No 54 |
| ShT 823 | M V Q E K | Seq ID No 55 | S K K Q | Seq ID No 56 |
| ShT 824 | D Y F Q T | Seq ID No 57 | R H Y S | Seq ID No 58 |

Table 3. Amino acid sequences of clones exhibiting cytotoxic activity CAMA-1 (clones recovered from a 60% doping level library). Loops 1 and 2 represent the same B subunit residues indicated in Table 1.

EXAMPLE 5

Assessment of Cycling of Cell Surface Molecules Targeted by Toxin Variants

It was found that the susceptibility of SK-BR-3 cells to the various mutants changed as a function of cell passages. FIG. 4 depicts this phenomenon for the toxin variant derived from clone 506. FIG. 4 shows the effect of variant 506 on passage 34 (♦), 40 (■), 56 (▲), and 68 (▼); and for the effect of native ShT on passages 40 (□), 56 (Δ), and 59 (○). The passage number represents the number of passages of the SK-BR-3 cell line in culture starting at passage #24 as defined by the American Type Culture Collection. Each point represents the percent cell viability calculated from the average of experiments performed in triplicate. The $CD_{50}$ for this ShT mutant ranged in values from 3.5 nM to >290 nM depending on the passage number of the SK-BR-3 cell line. The screen thus recorded the rapid and transient nature of selected surface markers on SK-BR-3 cells even in the case of a relatively clonal population of cells. Interestingly, the change in sensitivity of SK-BR-3 cells towards ShT-506 is a random event in relation to passage number (FIG. 5). The targeted cell line (starting at passage #24; ATTC) cycled from being resistant to ShT variant 506 at passage #32, to sensitive at passages #34 and #40, to being almost resistant again by passage #56 and finally reverting to being sensitive to the action of ShT variant 506 by passages #63 and #68. In contrast, SK-BR-3 cells remain resistant to the action of the native toxin over a similar range of cell passages, indicating that cell surface molecule CD77 remains stable over time. For example, FIG. 5 illustrates the difference in cell viability observed when SK-BR-3 cells were exposed to a 14 nM solution of either the native ShT (●) or the ShT variant 506 (○) at various cell passage numbers (each point represents the percent cell viability calculated from the average of experiments performed in triplicate).

This phenomenon suggests that the surface expression of CD77 is more regulated than the marker recognized by ShT variant 506. Differences in the cytotoxicity of ShT-506 toward SK-BR-3 cells were observed for more than 100 passages of the cell line, all performed under identical growth conditions (results not shown). Screening of the libraries of these variants thus provided a valuable source of probes to study the expression and rapid cycling of cell surface molecules. Other types of studies could exploit this feature of the libraries of the present invention. For example, collections of ShT variants could serve to phenotypically define differentiation events leading to the acquisition of metastatic potential of tumor cells, or to study the development of hematopoietic cell lineages.

Figure 4:
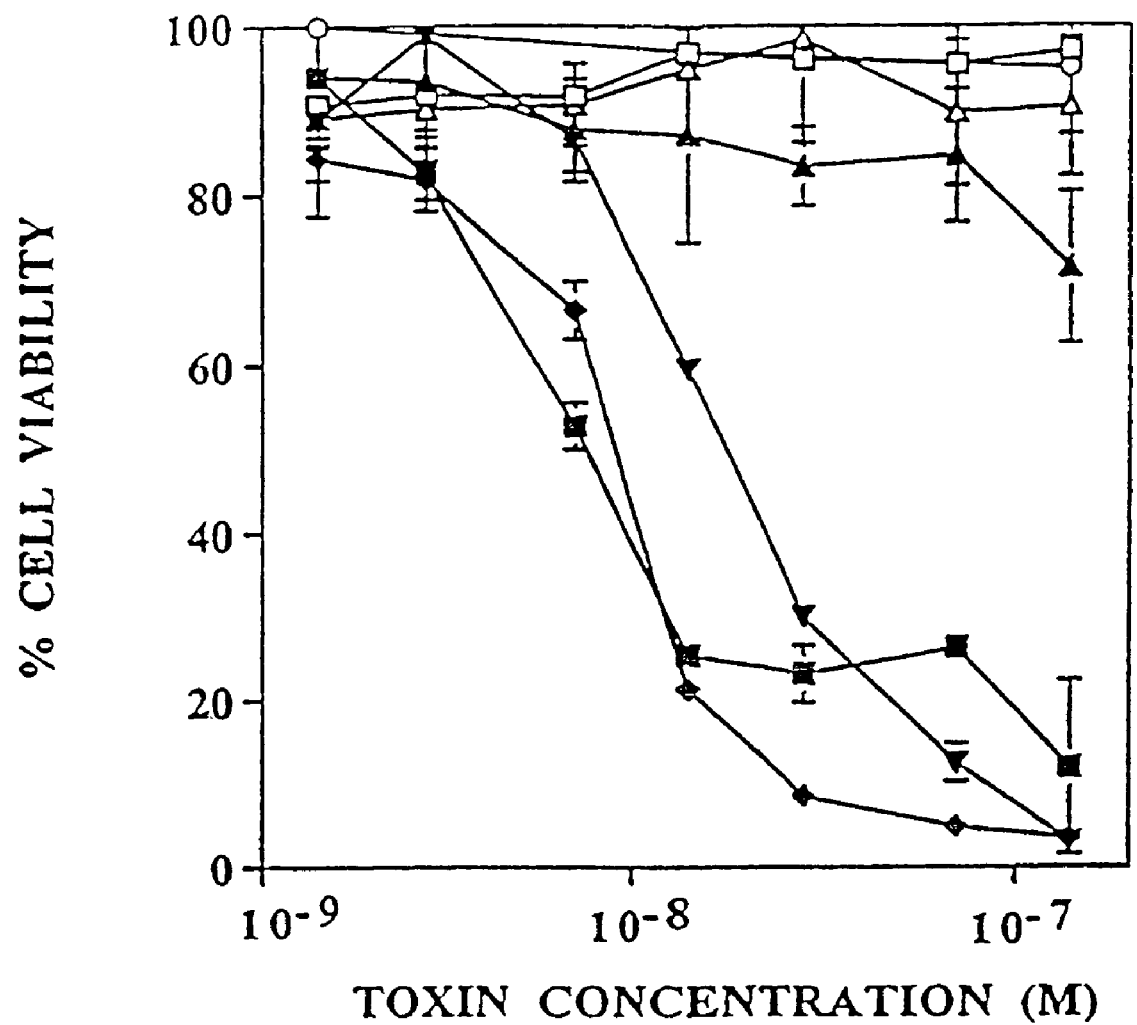
FIG. 4 is a graph showing cytotoxicity curves showing the ability of ShT variant 506 to kill SK-BR-3 cells on passage 34 (◆), 40 (■), 56 (▲), and 68 (▼); and for the effect of native ShT on passages 40 (□), 56 (Δ), and 59 (○).
Figure 5:
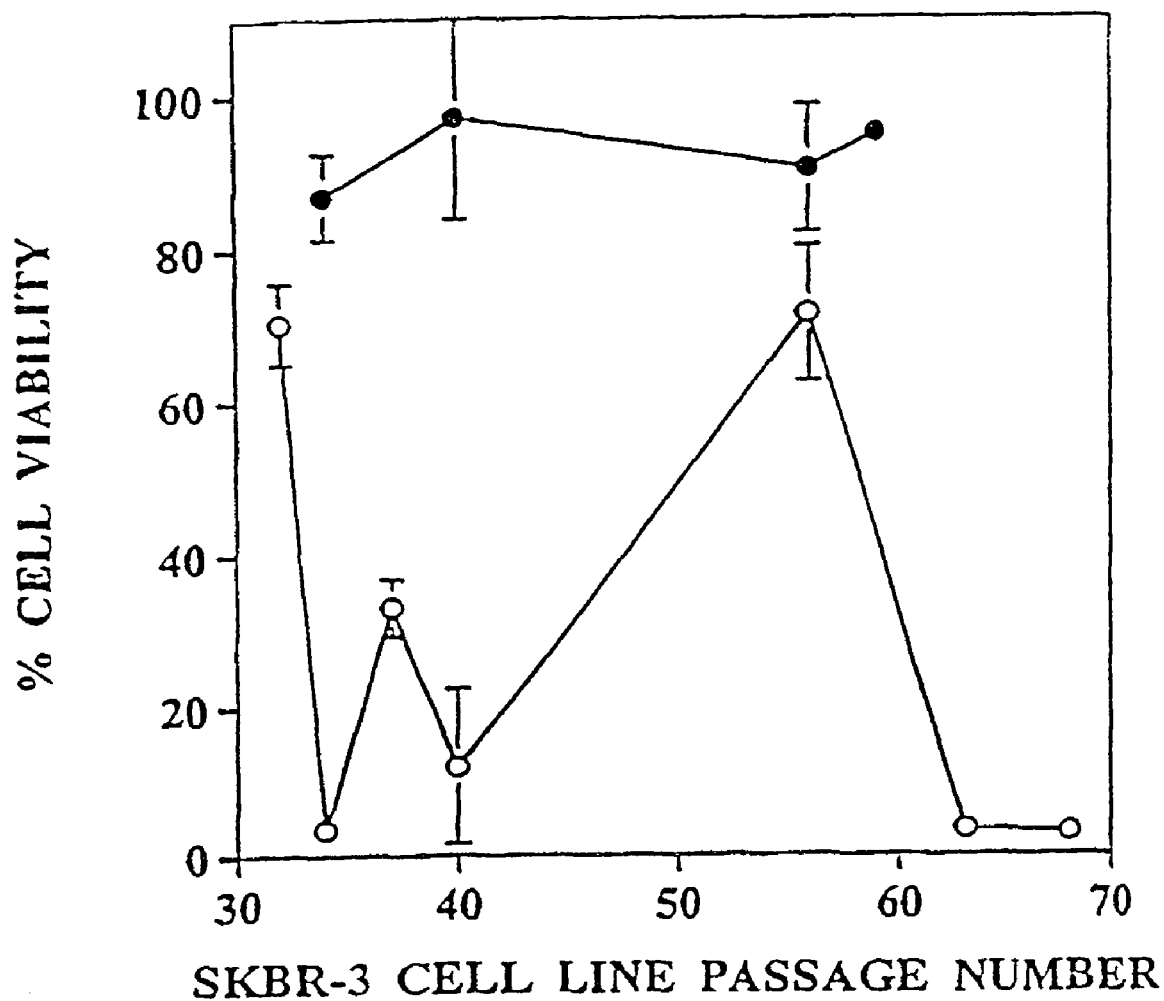
FIG. 5 is a graph showing the difference in cell viability observed when SK-BR-3 cells were exposed to a 14 nM solution of either the native ShT (●) or the ShT variant 506 (○) at various cell passage numbers.
Figure 6:
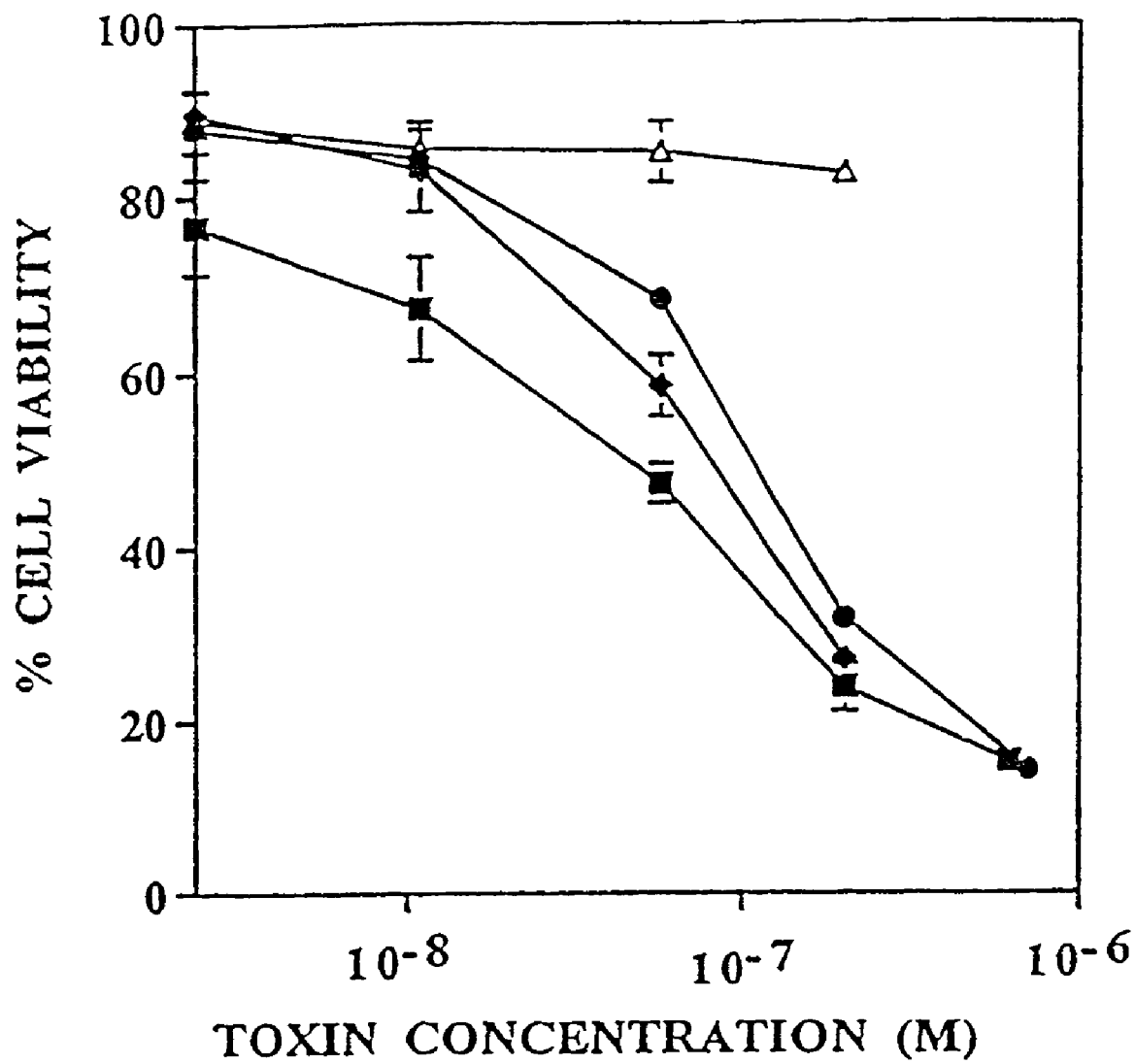
FIG. 6 is a graph showing the ability of three ShT variants (native toxin (Δ); ShT variant 122 (◆); ShT variant 126 (●); ShT variant 824 (■) identified which kill CAMA-1 cells.

The fact that most tumours are heterogeneous suggests that a large number of candidate toxins should be identified, perhaps to be administered as a cocktail in therapy. This fact underscores the power of the described approach, since a single toxin template can be screened for many potential specificities, whereas other agents such as immunotoxins have specificity only for cells exhibiting their target receptor. The concept of specificity also assumes that the expression of a targeted cell surface marker remains constant within a cell population. Results presented in FIG. 4 would argue against the validity of this hypothesis. The results herein demonstrate the ease with which one can identify a collection of toxin mutants cytotoxic toward a relatively homogeneous cell population by the use of this invention. Searches based on cytotoxicity assays are amenable to high throughput screening strategies and thus may allow a more thorough exploration of variant toxin libraries to find such families of toxin mutants. In the context of ex vivo purging situations the utility of toxin variants can be readily assessed by exposing bone marrow cells or peripheral stem cells to these agents and observing the level of reconstitution of haematopoietic cell lineages using flow cytometry under in vitro or in vivo settings (transplantation experiments in SCID, NOD/SCID mice, for example; ref. 14). The initial selection of breast cancer cell lines SK-BR-3 and CAMA-I as the population of screening cells used with the ShT library searches stems from the fact that most autologous bone marrow transplants (AB-MTs) or peripheral stem cell transplantations are presently performed on breast cancer patients, and that an ex vivo purging of their stem cells may prove beneficial in terms of the patient's long-term survival (13,106-107). The requirement for a uniquely selective agent for cancer cells, a major concern in the design of in vivo treatment strategies, is greatly reduced, since one or more mutant toxins may be clinically useful as long as the targeted surface marker is absent on human stem cells.

Analogies can be drawn between the structure of antibodies and ShT variants in terms of their ligand binding properties. Antibodies harbour two antigen combining sites while ShT B subunit pentamers possess at least five identical ligand binding domains. Both structural entities possess a conserved scaffold of β-strands linked by loop regions which together define their receptor binding domains. As in the case of antibody combining sites, B subunit variants may thus bind to a spectrum of molecular entities such as proteins, peptides, nucleic acids or even organic moieties rather than to sugars or glycolipids (such as CD77). However, the diversity of toxins derived from the libraries of the invention is not biased by genetic recombination and somatic mutations which dictate antibody repertoire. The vast potential for receptor-binding diversity present in the library highlights the fact that as the degeneracy of the library increases, so does the diversity of molecules on the cell surface available as ligands to mutated B-subunits.

EXAMPLE 6

Use of a Mutant Toxin to Develop a Diagnostic Tool

After selecting a heteromeric protein toxin and generating a library of microorganism clones producing variant protein toxins from the heteromeric protein toxin, the library is then screened against a target cell by the methods of the invention, i.e. by isolating clones or pools of clones producing the variant protein toxins, treating preparations of the target cell with the variant protein toxins and selecting a cytotoxic mutant protein or pool of cytotoxic mutant proteins that inhibits or kills the target cell. The genes producing the cytotoxic mutant protein or pool of proteins are manipulated to endogenously produce detectable markers. A diagnostic probe is thus constructed for detecting the presence of a cell surface marker by incorporating, by any means known in the art, a marker DNA encoding for a detectable marker into the binding subunit DNA sequence(s) of the cytotoxic mutant protein or pool of proteins, and generating diagnostic probes from the diagnostic DNA sequence. The present inventors have used green-fluorescent protein (GFP) from the jellyfish *Aequorea victoria* as a fluorescent marker for such diagnostic probes. This marker is useful in a variety of organisms ranging from bacteria to higher plants and animals (Tsein, R Y, 1998, *Annu Rev Biochem,* 67:509-44; Chalfie, M., Tu, Y., Euskirchen, G., Ward, W. W., and Prasher, D. C., 1994, *Science.* 263:802-805). Formation of the fluorescent chromophore is species independent and the gene product is easily detectable by its intense fluoresence (Prasher, D C, 1995, *Trends Genet,* 1995, August, 11(8):320-3). It is useful for monitoring gene expression in vivo, in situ, and in real time (Rizzuto R. et al, 1998, *Trends Cell Biol,* July, 8(7):288-92). When expressed in either eukaryotic or prokaryotic cells, GFP gives forth a bright green fluorescence. GFP fluoresces in the absence of any other intrinsic or extrinsic proteins, substrates, or cofactors. Fluorescence is stable, species-independent, and in some cases can be monitored noninvasively in living cells and whole animals (Chalfie, M., et al., supra).

In light of the demonstrated utility of the invention, a person skilled in the art will appreciate that the method can be applied to other cells with the expectation that useful therapeutic and diagnostic molecules will be identified. With numerous target sites on cells, it is expected that a large number of mutant toxins will be found with cytotoxic activity.

REFERENCES

1. Merritt, E. A., and Hol, W. G. J. (1995) Curr. Opin. Struct. Biol. 5:165
2. Olsnes, S, and Sandvik, K. (1988) in *Immunotoxins* pp. 39-73, Kluwer Academic, Boston.
3. Sandvik, K., Dubinina, E., Garred, O., et al. (1992) Biochem. Soc. Trans. 20:724
4. Stein, P. E., Boodhoo, A., Tyrell, G. J., et al. (1992) Nature. 355:748.
5. Fraser, M. E., Chernaia, M. M., Kozlov, Y. V. et al. (1994) Nature Struct. Biol. 1:59
6. Sixma, T. K., S. E. Pronk, K. H. Kalk, et al. (1991) Nature, 351:371
7. Sixma, T. K., S. E. Pronk, K. H. Kalk, et al. (1992) Nature, 355:561

8. Stein, P. E., Boodhoo, A., Armstrong, G. D., Cockle, et al. (1994) Structure 2:45
9. Allured, V. S., R. J. Collier, et al. (1986) Proc. Natl. Acad. Sci., 83:1320
10. Choe, S., Bennett, M., Fujii, G., et al. (1992) Nature 357:216
11. Monfort, W., Villafranca, J. E., Monzingo, A. F., et al. (1987) J. Biol. Chem. 262:5398
12. Rutenber, E., Ready, M., and Robertus, J. D. (1987) Nature 326:624
13. Saleh, M. T., Ferguson, J., Boggs, J. M., and Gariépy, J. (1996) Biochemistry 35:9325
14. LaCasse, E. C., Saleh, M. T., Patterson, et al. (1996) Blood, 88: 1561
15. Ramotar, K., Boyd, B., Tyrrell, G., Gariépy, J., et al. (1990) Biochem. J. 272:805
16. Boyd, B., Richardson, S., and J. Gariépy (1991) Infect. Immun. 59:750
17. Saleh, M., and Gariépy, J. (1993) Biochemistry 32:918
18. Sheldon, K, Liu, D., et al. (1995) Proc. Natl. Acad. Sci. USA 92:2056
19. Ashkenazi, S. (1993) Annu. Rev. Med. 44:11
20. Fontaine, A., Arondel, J., and Sansonetti, P. J. (1988) Infect. Immun. 56:3099
21. Karmali, M. A. (1989) Clin. Microb. Rev. 2: 15
22. Condari. H. (1903) Dtsch Med Wochenschr 29:26
23. O'Brien, A. D., and Holmes, R. K. (1987) Microb. Rev. 51:206
24. Konowalchuk, J., Speirs, J. I., and Stavric, S. (1977) Infect. Immun. 18:775
25. Marques, L. R. M., Moore, M. A., Wells, J. G., et al. (1986) J. Infect. Dis. 153:338
26. Strockbine, N. A., Marques, L. R. M., et al. (1986) Infect. Immun. 53:135
27. Oku, T., Yutsudo, T., Hirayama, T., et al. (1989) Microb. Pathog. 6:113
28. Marques, L. R. M., Peiris, J. S. M., Cryz, S. J., and O'Brien, A. D. (1987) FEMS Lett. 44:33
29. Olsnes, S., Reisbig, R., and Eiklid, K. (1981) J. Biol. Chem. 256:8732
30. Seidah, N. G., Donohue-Rolfe, A., Lazure, C., et al. (1986) J. Biol. Chem. 261:13928
31. Strockbine, N. A., Jackson, M. P., Sumg, L. M., et al. (1988) J. Bacteriol. 170: 116
32. De Grandis, S., Ginsberg, J., Toone, M., et al. (1987) J. Bact. 169:4313
33. Calderwood, S. B., Auclair, F., et al. (1987) Proc. Natl. Acad. Sci. (U.S.A.) 84:4364
34. Jackson, M. P., Newland, J. W., et al. (1987) Microb. Pathog. 2:147
35. Jackson, M. P., Neill, R. J., O'Brien, A. D., et al. (1987) FEMS Microb. Lett. 44:109
36. Lindberg, A. A., Brown, J. E., Stromberg, N., et al. (1987) J. Biol. Chem. 262:1779
37. Lingwood, C. A., Law, H., Richardson, S., et al. (1987) J. Biol. Chem. 262:8834
38. Eiklid, K., and Olsnes, S. (1983) Infect. Immun. 42:771
39. Jacewicz, M., and Keusch, G. T. (1983) J. Infect. Dis. 148:844
40. Sandvig, K., Olsnes, S., Brown, J. E., et al. (1989) J. Cell Biol. 108:1331
41. Endo, Y, Tsurugi, K, Yutsudo, T., Takeda, Y, et al. (1988) Eur. J. Biochem. 171:45
42. Saxena, S. K., O'Brien, A. D., and Ackerman, E. J. (1989) J. Biol. Chem. 264:596
43. Brown, J. E., Obrig, T. G., Ussery, M. A., and Moran, T. P. (1986) Microb. Pathog. 1:325
44. Igarashi, K., Ogasawara, T, Ito, K, Yutsudo, T., and Takeda, Y. (1987) FEMS lett. 44: 91
45. Ogasawara, T., Ito, K., Igarashi, K., Yutsudo, T., et al. (1988) Microb. Pathog. 4:127
46. Gottstein, C., Winkler, U., Bohlen, H., Diehl, U., and Engert, A. (1994) Ann. Oncol. 5:S97
47. Vallera, D. A. (1994) Blood, 83:309
48. Sandvik, K., Garred, O., Prydz, K., Kozlov, J. V., et al. (1992) Nature 358:510
49. Brown, J. E., M. A. Ussery, S. H. Leppla, and S. W. Rothman (1980) FEBS Lett., 117:84
50. Garred, O., Dubinina, E., Holm, P. K., Olsnes, S., et al. (1995) Exp. Cell Res. 218:39
51. Magnusson, S., Kjeken, R., and Berg, T. (1993) Exp. Cell Research 205:118
52. Reisbig, R., S. Olsnes, and K. Eiklid (1981) J. Biol. Chem. 256:8739
53. Frankel, A., Schlossman, D., Welsh, P., Hertler, A., et al. (1989) Mol. Cell Biol. 9:415
54. Deresiewicz, R. L., Calderwood, S. B., Robertus, J. D. et al. (1992) Biochemistry 31:3272
55. Ausubel, F. M., et al. (1994) Current Protocols in Molecular Biology, Vol. 2, Chapt. 13
56. Murray, L. J., Habeshaw, J. A., Wiels, J., Greaves, M. F. (1985) Int. J. Cancer 36:561
57. Mangeney M, Richard Y, Coulaud D, Tursz T, Wiels J (1991) Eur J. Immunol. 21:1131
58. Schwartz-Albiez, R., Dörken, B., Möller, P., et al. (1990) Int. Immunol. 2:929
59. Oosterwijk, E., Kalisiak, A., Wakka, J. C., et al. (1991) Int. J. Cancer 48:848
60. Kalisiak, A., Minniti, J. G., Oosterwijk, E., et al. (1991) Int. J. Cancer 49:837
61. Taga, S., Mangeney, M., Tursz, T., amd Wiels, J. (1995) Int. J. Cancer 61:261
62. Gordon, J., Mellstedt, H., Åman, P., et al. (1983) Blood 62:910
63. Ohyama, C., Fukushi, Y., Satoh, M., Saitoh, S., et al. (1990) Int. J. Cancer 45:1040
64. Cohen, A., Madrid-Marina, V., Estrov, Z., et al. (1990) Intern. Immunol. 2:1
65. Ghetie, M.-A, Richardson, A., Tucker, T., et al. (1991) Cancer Research 51:5876
66. Keating, A, and Toor, P. (1990) Meth Molec Biol 5:331
67. Quito, F. L., Beh, J., Bashayan, O., Basilico, C., and Basch, R. S. (1996) Blood 87:1282
68. Banchereau, J., and Rousset, F. (1991) Nature 353:678
69. Planken, E. V., Willemze, R., and Kluin-Nellemans, J. C. (1996) Leukemia Lymphoma 22:229
70. Schultze, J. L., Cardoso, A. A., Freeman G. J., et al. (1995) Proc. Natl. Acad. Sci. USA 92:8200
71. Johnson, P. W. M., Watt, S. M., Betts, D. R., et al. (1993) Blood 82:1848
72. Planken, E. V., Dijkstra, N. H., Willemze, R., et al. (1996) Leukemia 10:488
73. Banchereau, J., De Paoli, P., Valle, A., Garcia, E., and Rousset, F. (1991) Science 25:70
74. Burdin, N., Galibert, L., Garrone, P., Durand, I., et al. (1996) J. Immunol. 156: 4107
75. Galibert, L., Burdin, N., Barthélémy, C., Meffre, G., et al. (1996) J. Exp. Med. 183:2075
76. Rousset, F., Garcia, E., Defrance, T., et al. (1992) Proc. Natl. Acad. Sci. USA 89:1890
77. Levy, Y., and Brouet, J.-C. (1994) J. Clin. Invest. 93:424
78. Toellner, K.-M., Scheel-Toellner, D., Sprenger, R., et al. (1995) Cytokine 7:344

79. Tweedale, M. E., Lim, B., Jamal, N., Robinson, J., et al. (1987) Blood 69:1307
80. Chang, H., Messner, H. A., Wang, X.-H., Yee, C., et al. (1992) J. Clin. Invest. 89, 1014
81. Chang, H., Leder, S., Cook, V. A., Patterson, B., et al. (1992) Leukemia Lymphoma 8:129
82. Chang, H., Blondal, J. A., Benchimol, S., et al. (1995) Leukemia Lymphoma 19:165
83. Cattoretti, G., Chang, C.-C., Cechova, K., Zhang, J., et al. (1995) Blood 86:45
84. Miltenyi, S., Müller, W., Weichel, W., and Radbruch, A. (1990) Cytometry 11:231
85. Jackson, M. P., Wadolkowski, E. A., et al. (1990) J. Bacteriol. 172:653
86. Perera, L. P., Samuel, J. E., et al. (1991) J. Bacteriol. 173, 1151-1160.
87. Tyrrell, G. J., Ramotar, K., Toye, B., et al. (1992) Proc. Natl. Acad. Sci. USA 89:524
88. Jemal, C., Haddad, F. E., Begum, D., and Jackson, M. P. (1995) J. Bacteriol. 177:3128
89. Clark, C., Bast, D., Sharp, A. M., Sthilaire, P. M., et al. (1996) Mol. Microbiol. 19:891
90. Nyholm, P.-G., Brunton, J. L., et al. (1995) Int. J. Biol. Macromol. 17: 199
91. Nyholm, P.-G., Magnusson, G., et al. (1996) Chemistry and Biology 3:263
92. Graham, R. W., Greenwood, J. M., et al. (1995) Gene 158:51
93. Hill, D. E., Oliphant, A. R. and Struhl, K. (1987) Meth. Enz. 155:558
94. Hermes, J. D., Parekh, S. M., et al. (1989) Gene 84:143
95. Reidhaar-Olson, J. F., Bowie, J. U., et al. (1991) Meth. Enz. 208:564
96. Del Río, G., Osuna, J. and Soberón, X. (1994) Biotechniques 17:1132
97. Deng, W. P. and Nickoloff, J. A. (1992) Anal. Biochem. 200:81
98. McCormick, M. (1987) Meth. Enz. 151:445
99. Yamaizumi, M., Mekada, E., Uchida, T. and Okada, Y. (1978) Cell 15:245-250
100. Eiklid, K., Olsnes, S., and Pihl, A. (1980) Esp. Cell Res. 126:321-326
101. Rashtchian, A., Thornton, C. G., and Heidecker, G. (1992) PCR Methods and Applications 2:124-130.
102. M. Mangeney, Cancer Res. 53, 5314 (1993).
103. S.-C. Li, S. K. Kundu, R. Degasperi, Y.-T. Li, Biochem J. 240, 925 (1986).
104. K H. Farkas-Himsley, R. Hill, B. Rosen, S. Arab, C. A. Lingwood, Proc. Natl. Acad. Sci. USA 92, 6996 (1995).
105. J.-L. Kang, E. Rajpert-De Meyts, J. Wiels, N. E. Skakkabaek, Virchows Arch. 426, 369 (1995).
106. Vandat, K. Antman, Curr. Op. Hematol. 4, 381 (1997).
107. A V. Rizzoli, C. Carlo-Stella, Crit. Rev. Oncol./Hematol. 26, 101 (1997).

SEQUENCE LISTING

<160> NUMBER OF SEQ ID NOS: 58

<210> SEQ ID NO 1
<211> LENGTH: 293
<212> TYPE: PRT
<213> ORGANISM: Shigella dysenteriae

<400> SEQUENCE: 1

```
Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ser Gly Asp Asn
         35                  40                  45

Leu Phe Ala Val Asp Val Arg Gly Ile Asp Pro Glu Glu Gly Arg Phe
     50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
```

```
                165                 170                 175
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
        290

<210> SEQ ID NO 2
<211> LENGTH: 69
<212> TYPE: PRT
<213> ORGANISM: Shigella dysenteriae

<400> SEQUENCE: 2

Thr Pro Asp Cys Val Thr Gly Lys Val Glu Tyr Thr Lys Tyr Asn Asp
 1               5                  10                  15

Asp Asp Thr Phe Thr Val Lys Val Gly Asp Lys Glu Leu Phe Thr Asn
            20                  25                  30

Arg Trp Asn Leu Gln Ser Leu Leu Leu Ser Ala Gln Ile Thr Gly Met
        35                  40                  45

Thr Val Thr Ile Lys Thr Asn

-continued

```
<223> OTHER INFORMATION: nis a, c, g or t
<220> FEATURE:
<221> NAME/KEY: misc_feature
<222> LOCATION: (70)..(71)
<223> OTHER INFORMATION: nis a, c, g or t
<220> FEATURE:
<221> NAME/KEY: misc_feature
<222> LOCATION: (73)..(74)
<223> OTHER INFORMATION: nis a, c, g or t
<220> FEATURE:
<221> NAME/KEY: misc_feature
<222> LOCATION: (76)..(77)
<223> OTHER INFORMATION: nis a, c, g or t
<400> SEQUENCE: 3
aaggtggagt atacaaaata taatnnsnns nnsnnsnnsa cagttaaagt gggtgataaa     60
gaattannsn nsnnsnnstg gaatcttcag tctc                                 94

<210> SEQ ID NO 4
<211> LENGTH: 128
<212> TYPE: DNA
<213> ORGANISM: artificial
<220> FEATURE:
<223> OTHER INFORMATION: primer
<400> SEQUENCE: 4
tacgtactgc agctcgagtc aacgaaaaat aacttcgctg aatccaccgc cattatggca     60
cgcgttagtt ttaatggtta cagtcatacc ggtaatttgc gcactgagaa gaagagactg    120
aagattcc                                                             128

<210> SEQ ID NO 5
<211> LENGTH: 15
<212> TYPE: DNA
<213> ORGANISM: Shigella dysenteriae
<400> SEQUENCE: 5
aatgatgacg atacc                                                      15

<210> SEQ ID NO 6
<211> LENGTH: 12
<212> TYPE: DNA
<213> ORGANISM: Shigella dysenteriae
<400> SEQUENCE: 6
tttaccaaca ga                                                         12

<210> SEQ ID NO 7
<211> LENGTH: 5
<212> TYPE: PRT
<213> ORGANISM: Shigella dysenteriae

<400> SEQUENCE: 7

Asn Asp Asp Asp Thr
1               5

<210> SEQ ID NO 8
<211> LENGTH: 4
<212> TYPE: PRT
<213> ORGANISM: Shigella dysenteriae

<400> SEQUENCE: 8

Phe Thr Asn Arg
1
```

```
<210> SEQ ID NO 9
<211> LENGTH: 15
<212> TYPE: DNA
<213> ORGANISM: artificial
<220> FEATURE:
<223> OTHER INFORMATION: mutant fragment from Shigella dysenteriae

<400> SEQUENCE: 9
aacgaggagg agacg                                                    15

<210> SEQ ID NO 10
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 10

Asn Glu Glu Glu Thr
1               5

<210> SEQ ID NO 11
<211> LENGTH: 12
<212> TYPE: DNA
<213> ORGANISM: artificial
<220> FEATURE:
<223> OTHER INFORMATION: mutant fragment from Shigella dysenteriae

<400> SEQUENCE: 11
ttcgcgaaca gc                                                       12

<210> SEQ ID NO 12
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 12

Phe Ala Asn Asn
1

<210> SEQ ID NO 13
<211> LENGTH: 15
<212> TYPE: DNA
<213> ORGANISM: artificial
<220> FEATURE:
<223> OTHER INFORMATION: mutant fragment from Shigella dysenteriae

<400> SEQUENCE: 13
aacgagcagg acacc                                                    15

<210> SEQ ID NO 14
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 14

Asn Glu Gln Asp Thr
1               5

<210> SEQ ID NO 15
<211> LENGTH: 12
<212> TYPE: DNA
<213> ORGANISM: artificial
```

-continued

```
<220> FEATURE:
<223> OTHER INFORMATION: mutant fragment from Shigella dysenteriae
<400> SEQUENCE: 15
ttcgcgaaca gc 12

<210> SEQ ID NO 16
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 16

Phe Thr His Arg
1

<210> SEQ ID NO 17
<211> LENGTH: 15
<212> TYPE: DNA
<213> ORGANISM: artificial
<220> FEATURE:
<223> OTHER INFORMATION: mutant fragment from Shigella dysenteriae
<400> SEQUENCE: 17
aaggacgacg cgagg 15

<210> SEQ ID NO 18
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 18

Lys Glu Asn Glu Ser
1 5

<210> SEQ ID NO 19
<211> LENGTH: 11
<212> TYPE: DNA
<213> ORGANISM: artificial
<220> FEATURE:
<223> OTHER INFORMATION: mutant fragment from Shigella dysenteriae
<400> SEQUENCE: 19
ttcgcgacaa c 11

<210> SEQ ID NO 20
<211> LENGTH: 15
<212> TYPE: DNA
<213> ORGANISM: artificial
<220> FEATURE:
<223> OTHER INFORMATION: mutant fragment from Shigella dysenteriae
<400> SEQUENCE: 20
aaggacgacg cgagg 15

<210> SEQ ID NO 21
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 21
```

Lys Asp Asp Ala Arg
1               5

<210> SEQ ID NO 22
<211> LENGTH: 12
<212> TYPE: DNA
<213> ORGANISM: artificial
<220> FEATURE:
<223> OTHER INFORMATION: mutant fragment from Shigella dysenteriae

<400> SEQUENCE: 22
ttgacccaga gg 12

<210> SEQ ID NO 23
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 23

Leu Thr Gln Arg
1

<210> SEQ ID NO 24
<211> LENGTH: 15
<212> TYPE: DNA
<213> ORGANISM: artificial
<220> FEATURE:
<223> OTHER INFORMATION: mutant fragment from Shigella dysenteriae

<400> SEQUENCE: 24
aaggacgacg acacg 15

<210> SEQ ID NO 25
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 25

Lys Asp Asp Asp Thr
1 5

<210> SEQ ID NO 26
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 26

Glu Phe Thr Gly
1

<210> SEQ ID NO 27
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 27

Phe Thr Lys Ser
1

```
<210> SEQ ID NO 28
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 28

Thr Thr Asp Asp Pro
1               5

<210> SEQ ID NO 29
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 29

Gly Thr Arg Gly
1

<210> SEQ ID NO 30
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 30

Leu Thr Asn Gly
1

<210> SEQ ID NO 31
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 31

Leu Pro Asn Arg
1

<210> SEQ ID NO 32
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 32

Phe Thr Asn Cys
1

<210> SEQ ID NO 33
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 33

Lys Glu Asp Glu Ser
1               5
```

-continued

```
<210> SEQ ID NO 34
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 34

Leu Thr Lys Arg
1

<210> SEQ ID NO 35
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 35

Leu Thr Lys Ser
1

<210> SEQ ID NO 36
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 36

Tyr Asp Asp Asn Pro
1               5

<210> SEQ ID NO 37
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 37

Leu Thr Asn Ser
1

<210> SEQ ID NO 38
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 38

Lys Lys Glu Glu Pro
1               5

<210> SEQ ID NO 39
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 39

Cys Ala Asn Arg
1

<210> SEQ ID NO 40
```

-continued

```
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 40

Leu Thr Asn Arg
1

<210> SEQ ID NO 41
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 41

Cys Leu Leu Asn Gly
1               5

<210> SEQ ID NO 42
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 42

Tyr Gln Glu Pro
1

<210> SEQ ID NO 43
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 43

Gln Gly Leu Gln Leu
1               5

<210> SEQ ID NO 44
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 44

Thr Leu Thr Gly
1

<210> SEQ ID NO 45
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 45

Thr Gly Ala Thr Met
1               5

<210> SEQ ID NO 46
<211> LENGTH: 4
```

```
<212> TYPE: PRT
<213> ORGANISM: artificial
<220> FEATURE:
<223> OTHER INFORMATION: mutant fragment from Shigella dysenteriae

<400> SEQUENCE: 46

Pro Thr Gly Ile
1

<210> SEQ ID NO 47
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 47

Phe Arg Pro Ala Gly
1               5

<210> SEQ ID NO 48
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 48

Leu Arg Cys Gly
1

<210> SEQ ID NO 49
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 49

Pro Tyr Val Phe Leu
1               5

<210> SEQ ID NO 50
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 50

Met Val Ala Asn
1

<210> SEQ ID NO 51
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 51

Lys Ser Met Asp Gln
1               5

<210> SEQ ID NO 52
<211> LENGTH: 4
<212> TYPE: PRT
```

```
<213> ORGANISM: artificial
<220> FEATURE:
<223> OTHER INFORMATION: mutant fragment from Shigella dysenteriae

<400> SEQUENCE: 52

Leu Ser Lys Trp
1

<210> SEQ ID NO 53
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 53

Gln Gly Glu Tyr Gly
1               5

<210> SEQ ID NO 54
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 54

Ile Gln Glu Arg
1

<210> SEQ ID NO 55
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 55

Met Val Gln Glu Lys
1               5

<210> SEQ ID NO 56
<211> LENGTH: 4
<212> TYPE: PRT
<213> ORGANISM: artificial
<220> FEATURE:
<223> OTHER INFORMATION: mutant fragment from Shigella dysenteriae

<400> SEQUENCE: 56

Ser Lys Lys Gln
1

<210> SEQ ID NO 57
<211> LENGTH: 5
<212> TYPE: PRT
<213> ORGANISM: artificial
<220> FEATURE:
<223> OTHER INFORMATION: mutant fragment from Shigella dysenteriae

<400> SEQUENCE: 57

Asp Tyr Phe Gln Thr
1               5

<210> SEQ ID NO 58
<211> LENGTH: 4
<212> TYPE: PRT
<213> ORGANISM: artificial
```

-continued

```
<220> FEATURE:
<223> OTHER INFORMATION: mutant fragment from Shigella dysenteriae (B) preparing a diagnostic probe by labeling the selected cytotoxic mutant protein in a manner which maintains the ability of the binding domain or subunit of the selected cytotoxic mutant protein to specifically bind to the cell surface marker.

18. The method of claim 17, wherein the diagnostic probe is prepared by a method comprising:
 (i) preparing a diagnostic DNA sequence comprising a marker DNA encoding a detectable marker and a binding domain or subunit DNA sequence encoding the binding domain or subunit of the selected cytotoxic mutant protein; and
 (ii) expressing the diagnostic DNA sequence to generate a diagnostic probe.

19. A method for constructing diagnostic probes as claimed in claim 18 wherein said marker DNA codes for green-fluorescent protein (GFP).

20. The method of claim 17, further comprising the step of modifying the cytotoxic mutant protein or pool of proteins by dissociation or inactivation of the toxic domain or subunit of the cytotoxic mutant protein.

21. A method for making a targeted medicament for delivery to a target cell having a cell surface marker, said targeted medicament comprising a binding portion and a medicament portion comprising the step of:
 (A) identifying a binding subunit which binds to the cell surface marker by a process comprising the steps of
  (i) selecting a heteromeric protein toxin having a toxic domain or subunit and a binding domain or subunit, wherein the heteromeric protein toxin is a ribosome inactivating protein;
  (ii) incorporating mutations into DNA encoding the binding domain or subunit of the heteromeric protein toxin to produce a plurality of variant forms of the heteromeric protein toxin;
  (iii) generating a library of microorganism clones producing variant forms of the heteromeric protein toxin;
  (iv) screening the variant forms of the heteromeric protein toxin of said library against a population of screening cells by (a) isolating clones or pools of clones producing said variant forms of the heteromeric protein toxin, (b) treating preparations of said population of screening cells with variant forms of the heteromeric protein toxin produced by the isolated clones or pools of clones, (c) observing the treated preparations of said population of screening cells for toxicity, and (d) selecting based on the observation of toxicity a cytotoxic mutant protein or pool of cytotoxic mutant proteins that inhibits or kills said population of screening cells to a greater extent than the wild-type cytotoxic protein, whereby said selected mutant protein or pool of proteins has receptor-binding specificity for the target cell population that is reflected by the observation of toxicity, wherein the screening cells are insensitive to the selected wild-type heteromeric protein toxin at a concentration used in the screening; and
  (v) determining the sequence of the binding domain or subunit of the selected cytotoxic mutant protein for use as the binding portion of the targeted medicament; and
 (B) combining the binding portion with the medicament portion.

22. The method of claim 21, wherein the binding portion and the medicament portion are combined by preparing a medicament DNA sequence comprising a medicinal DNA encoding a medicinal polypeptide for use as the medicament portion, and a binding domain or subunit DNA sequence encoding the binding portion, further comprising the step of expressing the medicament DNA sequence.

23. A method for making a nucleic acid sequence, or pool of nucleic acid sequences, encoding a cytotoxic mutant protein, or pool of cytotoxic mutant proteins, of a cytotoxic wild type protein said mutant protein or pool of proteins having receptor-binding specificity for a receptor that is different from the receptor to which the wild type protein has receptor binding specificity, comprising:
 (A) selecting a heteromeric protein toxin having a toxic domain or subunit and a binding domain or subunit, wherein the heteromeric protein toxin is a ribosome inactivating protein;
 (B) incorporating mutations into DNA encoding the binding domain or subunit of the heteromeric protein toxin to produce a plurality of variant forms of the heteromeric protein toxin;
 (C) generating a library of microorganism clones producing variant forms of the heteromeric protein toxin;
 (D) screening, the variant forms of the heteromeric protein toxin of said library against a population of screening cells by (i) isolating clones or pools of clones producing said variant forms of the heteromeric protein toxin, (ii) treating preparations of said population of screening cells with variant forms of the heteromeric protein toxin produced by the isolated clones or pools of clones, (iii) observing the treated preparations of said population of screening cells for toxicity, and (iv) selecting based on the observation of toxicity a cytotoxic mutant protein or pool of cytotoxic mutant proteins that inhibits or kills said population of screening cells to a greater extent than the wild-type cytotoxic protein, whereby said selected mutant protein or pool of proteins has the different receptor binding specificity that is reflected by the observation of toxicity, wherein the screening cells are insensitive to the selected wild-type cytotoxic heteromeric protein toxin at a concentration used in the screening; and
 (E) making additional copies of the nucleic acid sequence or pool of nucleic acid sequence encoding the selected cytotoxic mutant protein or pool of cytotoxic mutant proteins.

24. The method of claim 23, wherein the cells in the population of screening cells are eukaryotic.

25. The method of claim 24, wherein the cells in the population of screening cells are tumor cells.

26. The method of claim 25, wherein the tumor cells are breast cancer cells.

27. The method of claim 23, wherein the binding domain or subunit is derived from the B-subunit of either Shiga toxin and Shiga-like toxins, or homologous counterparts from *E. coli* heat labile enterotoxins, cholera toxin, pertussis toxin or the receptor binding, domain of ricin.

28. The method of claim 1, wherein in step B the mutations are randomly incorporated into the DNA encoding the binding domain or subunit of the heteromeric protein toxin.

* * * * *